United States Patent [19]
Hellenkamp

[11] Patent Number: 5,772,675
[45] Date of Patent: Jun. 30, 1998

[54] POSITIONING ASSEMBLY FOR RETAINING AND POSITIONING A CORNEA

[75] Inventor: Johann F. Hellenkamp, Miami, Fla.

[73] Assignee: Chiron Vision Corporation, Claremont, Calif.

[21] Appl. No.: 741,955

[22] Filed: Oct. 31, 1996

[51] Int. Cl.⁶ ...................................................... A61B 17/00
[52] U.S. Cl. ............................................................. 606/166
[58] Field of Search ............................... 606/1, 107, 166, 606/167, 4, 5, 161; 604/294

[56] References Cited

U.S. PATENT DOCUMENTS

| | | | |
|---|---|---|---|
| 3,074,407 | 1/1963 | Moon et al. | 606/166 |
| 4,688,570 | 8/1987 | Kramer et al. | 606/166 |
| 5,009,660 | 4/1991 | Clapham | 606/166 |
| 5,092,863 | 3/1992 | Schanzlin | 606/5 |
| 5,489,299 | 2/1996 | Schachar | 606/5 |

*Primary Examiner*—Michael Buiz
*Assistant Examiner*—William W. Lewis
*Attorney, Agent, or Firm*—Malloy & Malloy, P.A.

[57] ABSTRACT

An improved positioning assembly for positioning and holding a cornea of an eye during surgery comprising a positioning ring, a suction force operably coupled to the positioning ring to temporarily attach it to the eye and a suction enhancement member. The positioning ring includes a retention plate, having an aperture defined therein to receive the cornea of the eye and an interior rim disposed in surrounding relation about the aperture, and a flange member extending downwardly from the retention plate in spaced, surrounding relation to the aperture. The positioning ring further includes a vacuum port in fluid flow communication with a point radially interior of the flange member such that a suction force applied therethrough secures the positioning ring to the eye with the cornea protruding through the aperture. The suction enhancement member preferably comprises a resilient material segment structured to engage the positioning ring at a point radially interior of the flange member, and disposed to define a suction channel between the suction enhancement member and the positioning ring, which channel is in fluid flow communication with the vacuum port. A plurality of suction ports are preferably defined in the segment and in fluid flow communication with the suction channel. When a suction force is applied to the positioning ring, the suction enhancement member effects an improved vacuum seal substantially about the eye and further, prevents partial or complete occlusion of the suction force.

26 Claims, 2 Drawing Sheets

POSITIONING ASSEMBLY FOR RETAINING AND POSITIONING A CORNEA

BACKGROUND OF THE INVENTION

1. Field of the Invention

The present invention relates generally to a medical apparatus used during the performance of eye surgery and in particular, is directed towards a positioning assembly for retaining and positioning a patient's eye for cutting of the cornea during a surgical procedure, such as to correct for refractive error. More specifically, the present invention is specifically directed to achieving and maintaining an improved attachment of a positioning ring to the eyeball during surgery.

2. Description of the Related Art

The eye works on a principle very similar to that of a camera wherein the iris, or colored portion of the eye about the pupil, functions like a shutter to regulate the amount of light admitted to the interior of the eye. The cornea or clear window of the eye, and the lens, which is located behind the pupil, serve to focus the light rays from an object being viewed onto the retina at the back of the eye. The retina then transmits the image of the object viewed to the brain via the optic nerve. Normally, these light rays will be focused exactly on the retina, which permits the distant object to be seen distinctly and clearly. Deviations from the normal shape of the corneal surface however, produce errors of refraction in the visual process so that the eye becomes unable to focus the image of the distant object on the retina, with the result that one sees a blurred image.

About twenty years ago, such refractive errors could only be treated with eyeglasses or contact lens, both of which have well known disadvantages for the user. Since then, however, surgical operations have been developed to change the refractive condition of the eye. Several methods and special instruments have been designed for performing this kind of surgery, which are primarily directed to reshape the cornea. It will be appreciated that the goal of corneal reshaping is to modify the curvature of the cornea, i.e., either to flatten or increase its curvature depending on the patient's condition, so that light rays passing through the cornea will thereafter be refracted to focus or converge directly onto the retina, thereby permitting the patient to view a distant object clearly.

One such surgical operation is keratomileusis, which requires a precise reshaping of the cornea by cutting and separating a thin layer of corneal tissue, termed the corneal cap, by lathing that tissue and then, by suturing the reshaped corneal tissue back into place on the eye. Keratomileusis is viewed, however, as having several drawbacks, and consequently, has been abandoned in recent years. Automated Lamellar Keratectomy (ALK) is another surgical technique which developed as an outgrowth of keratomileusis. In an ALK procedure, the eye is typically first numbed by a drop of anesthetic, and then, a device having a ring shaped configuration is placed on the eye to carefully position the cornea (termed "centration" in the art) for being cut by a very fine microsurgical instrument known as a microkeratome. The microkeratome is generally a blade carrying device that must be manually pushed or mechanically driven in a cutting path across the ring shaped device to cut into the cornea. Under an ALK procedure to treat near-sightedness, the microkeratome is typically first used to cut and lift a thin layer of the cornea, instead of severing it, and second, to carry out a reshaping of the cornea by way of a second pass of the microkeratome over the cornea with the cutting element adjusted to pass therethrough at a desired and pre-determined corrective depth. Thereupon the thin, raised layer of corneal tissue is put back in place over the cornea for healing. Despite developments in the art utilizing a laser to carry out the step of re-shaping the cornea, the above-described ALK procedure for near-sightedness may still be followed in certain cases, depending on the depth of the corneal cut needed. Conversely, ALK procedures to treat far-sightedness, wherein the microkeratome is used to make a single cut, are generally no longer followed given the advances which have since occurred in the field.

From the foregoing, it will be appreciated that ALK procedures are considered to possess drawbacks, particularly in that the penetration of the microkeratome's cutting element into the cornea to a precise depth is critical and may not always be achieved. Thus, in more recent years, substantial advances have been made for correcting refractive errors of the eye utilizing a laser to reshape the cornea. One such procedure, known as Laser Intrastromal Keratomileusis, (LASIK), is currently considered optimal because it allows sculpting of the cornea without damaging adjacent tissues, and further, because with the aid of computers, the laser can be programmed by a surgeon to more precisely control the amount of tissue removed, and significantly, to permit more options for the reshaping of the cornea. Under LASIK procedures, the eye is still typically positioned within a ring shaped device and a microkeratome is typically first used to cut into the cornea so as to raise a thin layer of the cornea, prior to treatment with the laser to reshape the cornea. Still, however, and regardless of the procedure employed, great care and precision are of critical importance to the safety and success of the procedure.

The use of a device having a ring shaped configuration to hold the eyeball in place during a corneal reshaping surgery is well known in the art. Such devices are commonly attached to the eyeball temporarily by way of a suctioning force or vacuum. A typical suction ring device is depicted in FIG. 1 and is seen to include an annular, hollow ring, R, defining an aperture, K, which allows the cornea to be exposed, and an open bottom side that is applied to the surface of the eyeball around the cornea. The ring, R is seen to be in communication with a hollow suction tube, T which opens into the hollow open bottom side of the ring. Commonly known suction ring devices apply a vacuum to the ring R, via tube T, to the eyeball at a single point, P, illustrated in FIG. 2. When the suction ring is applied to the eyeball, with suction or a vacuum applied to the hollow tube, and thus, to the bottom of the ring, the suction ring attaches to the surface of the eyeball surrounding the cornea, with the suction force holding the ring in a reasonably secure fashion, to the eyeball. As a result, the suction ring has become a conventional device in ophthalmic practice, and it should be noted, is designed to be re-usable so as to accommodate a large number of patients over the course of its useful life.

Ophthalmologists have complained, however, that during surgery the vacuum seal, which attaches the suction ring device to the eyeball, may break on occasion. Although not a common occurrence, when the vacuum seal breaks, it is extremely serious in that the precise positioning or centration of the suction ring on the eyeball is lost. More specifically, a critical first step in performing corneal reshaping surgery is the accurate centration of the suction ring on the eye, in precise alignment with the optical axis, with the suctioning force applied to achieve a reliable vacuum seal to maintain the eyeball in the centrated position. If surgery on the eye is underway, with reshaping of the cornea in progress, and the vacuum seal breaks, there can be devastating consequences. Consequently, it is considered imperative that any cutting of the cornea be stopped immediately. Moreover, surgery on the eye should not resume as quite obviously, it is not feasible for the suction ring to be precisely re-aligned or re-centrated in its original position, and it is even more improbable that the cutting element can be precisely re-aligned with the cutting of the cornea already underway. Surgery in progress should therefore be stopped, and any cut portions of the cornea should be returned to a proper position on the eye, with the eye being permitted to heal over the course of three months, before surgery on that eye can be undertaken anew. It will therefore be appreciated that this situation is utterly undesirable for several reasons, but primarily because of the potentially devastating consequences to the patient.

One known factor which contributes to the occasional breakage of the vacuum seal attaching the suction ring to the eyeball is the partial or complete occlusion of the suction force being applied. Specifically, when a vacuum is applied to known suction ring devices during surgery, the vacuum necessarily acts on tissue about the eyeball and more particularly, a mucous membrane that lines the exposed surface of the eyeball known as conjunctiva. With many patients, this factor does not affect the surgery. Other patients, however, have a condition, generally known in the art as "chemosis", which can affect the surgery. Chemosis is a condition wherein fluids can exist under the conjunctiva of the eye such that during surgery, the action of the vacuum on the conjunctiva can cause it to pull away from the surface of the eyeball and towards the single vacuum focal point P of the suction ring. When this occurs, the vacuum can become completely or partially blocked, with the result that the vacuum seal is compromised and likely, broken. It will be recognized that the patient condition of chemosis is relatively uncommon and generally, will be detected before cutting of the cornea begins, and in that case, there is no untoward consequence for the patient. The concern for serious complications arises when surgical cutting of the cornea is underway at the time the vacuum seal breaks, such as by the effects of chemosis, explained above.

Another factor may also contribute to the occasional breakage of the vacuum seal which attaches the suction ring to the eyeball during surgery. Specifically, during surgery the action of the suction force may draw some mucus from the eye into the internal passages of the vacuum, such as into the hollow tube T, shown in FIGS. 1 and 2. Should this occur, it is unlikely to lead immediately to the occlusion of the vacuum. On the other hand, an effective cleaning of the suction ring's internal vacuum passages is tedious at best, and at worst, may not truly be possible. Consequently, any mucus which is drawn into the vacuum passages of the suction ring may remain there to harden in place. Over time then, it is possible for mucus to build-up and accumulate within the internal vacuum passages of a suction ring. A partial or complete occlusion of the suction force applied to the suction ring might eventually result during a subsequent surgery, and lead to a breakage of the vacuum seal.

A potential solution to the problem might be to apply the vacuum to known suction ring devices at more than a single vacuum point on the suction ring. However, the action of a suction force applied to the suction ring, even through a plurality of vacuum points thereabout, might still cause chemosis in that conjunctiva could still block one or more of the vacuum points. This is particularly true in that the suction force applied to the suction ring would likely remain undispersed and concentrated at the vacuum points. Additionally, the problem would persist of eye mucus becoming lodged within the interior vacuum passages of the suction ring. As has been described, a thorough cleaning of the suction ring's internal vacuum passages may not be possible, and even if it were possible, cleaning mucus out of the internal vacuum passages would be time consuming. This factor alone carries a negative economic impact in that only a smaller number of surgeries could be performed with the device in a single day.

Therefore, there remains a need in the art for a positioning assembly which not only retains and positions a cornea of patient's eye during surgery, but which has an improved ability to remain securely attached to the eyeball during surgery, without occlusion of the vacuum. Any such improved positioning assembly should be capable of functioning with known suction rings. It would be highly beneficial if any such improved positioning assembly were able to enhance the suction gripping ability of the suction ring device so as to offer a seal about the eye which is more resistant to being broken during surgery. Any such suction enhancement means would preferably provide a suction force substantially about the girth of the eyeball, if not entirely thereabout, instead of to a single point adjacent the eyeball, and further, would be structured to apply the suction force about the eyeball in a dispersed and uniform manner. Any such suction enhancement means would ideally prevent the effects of chemosis, that is, prevent conjunctiva from partially or completely blocking the suctioning force applied to the suction ring, and further, would ideally limit, if not prevent altogether, eye mucus from entering the interior vacuum passages of the suction ring during surgery.

SUMMARY OF THE INVENTION

The present invention is designed to satisfy the needs which remain in the art and is directed towards a positioning assembly for retaining and positioning a cornea of patient's eye for performance of a surgical procedure thereon. More specifically, the present invention is directed towards improving and preserving the vacuum seal between a suction ring, also known as a positioning ring, and an eyeball to which the ring is attached during surgery. While the present invention has application to any eye, it would typically be used on the human eye.

The positioning assembly of the present invention is seen to comprise suction enhancement means for use with a positioning ring and suctioning means operably coupled thereto. More specifically, the positioning assembly may include a positioning ring having a main body, which defines an aperture sized to receive and expose the cornea to be cut and which includes a flange member extending downwardly therefrom and generally about the aperture so as to define a generally open bottom side. The assembly may also comprise suctioning means operably coupled to the positioning ring for supplying a suction force to an undersurface thereof to temporarily attach the positioning ring to a portion of the eye surrounding the cornea to be cut during surgery. The suction enhancement means of the present invention are preferably structured and disposed to extend substantially about the aperture of the positioning ring and further, are disposed at least partially between the suctioning means of the positioning ring and the portion of the eye surrounding the cornea to be cut so as to define a suction channel. The suction enhancement means are additionally structured and disposed to maintain the suction channel generally free from mucus and other mucous tissue, which might otherwise completely or partially block the suction force applied through the positioning ring.

An object of the present invention is to provide a positioning assembly having an improved ability to prevent the vacuum seal, which attaches a positioning ring to the cornea of a patient's eye in a precisely controlled orientation for cutting during surgery, from being broken.

It is also an object of the present invention is to provide a positioning assembly which enhances the suction gripping ability of a positioning ring so as to more securely and more uniformly attach the positioning ring to an eyeball once a vacuum or suctioning force is applied during surgery.

Another object of the present invention is to provide a positioning assembly having suction enhancement means disposed substantially about the eyeball so as to evenly distribute the suction force about the eyeball and thereby, offer a more secure and more stable attachment to the eyeball during surgery.

An additional object of the present invention to provide an a positioning assembly having suction enhancement means structured and disposed to define a suction channel between the suctioning means and the eyeball to be cut during surgery, and further, to maintain the suction channel evacuated even in the presence of chemosis and/or mucous tissue which might otherwise effect an occlusion of the suction force being applied to the assembly.

An advantage of the present invention is that it offers a positioning assembly having an improved seal about the eye when a suctioning force is applied, which seal is highly resistant to being broken during surgery on the eye.

A feature of the suction enhancement means according to the present invention is the ability to be utilized with known suction ring devices.

Yet another object of the present invention is to provide a positioning assembly having suction enhancement means which can be easily introduced into as well as removed from the positioning ring for disposal, without damaging the positioning ring.

Another advantage of the present invention is that in offering removable suction enhancement means, it facilitates cleaning of the positioning ring.

Yet another advantage of the present invention is that the amount of time required to properly clean the positioning ring is reduced, thereby allowing a surgeon to use the positioning ring to perform a larger number of surgical procedures in a single day.

These and other objects, features and advantages of the present invention will become more readily apparent from the drawings and the detailed description which follows.

BRIEF DESCRIPTION OF THE DRAWINGS

For a fuller understanding of the nature of the present invention, reference should be had to the following detailed description taken in connection with the accompanying drawings in which:

FIG. 3-B is a front view of the suction enhancement means of the present invention in an alternative embodiment;

FIG. 3-C is a front view of the suction enhancement means of the present invention in yet another alternative embodiment;

Like reference numerals refer to like parts throughout the several views of the drawings.

DETAILED DESCRIPTION OF THE PREFERRED EMBODIMENT

Figure 4:
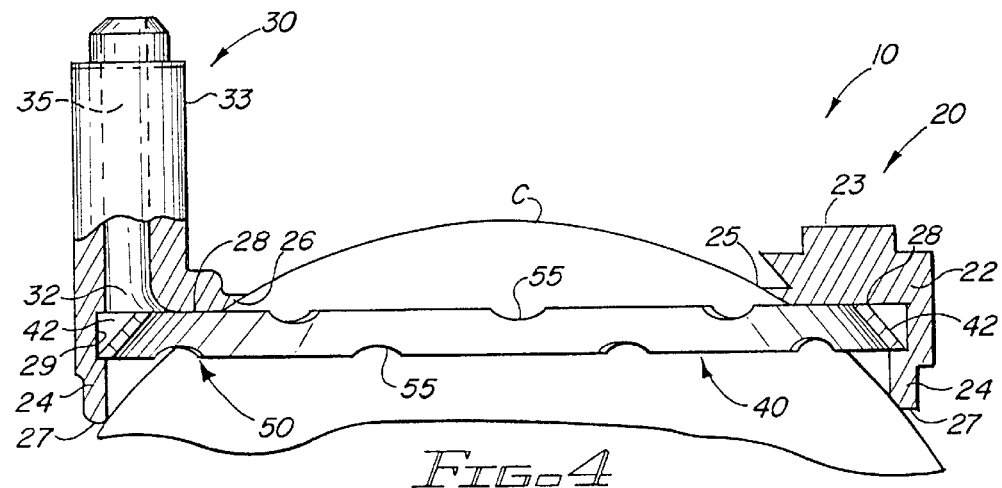
FIG. 4 is a partial cross sectional view of the improved positioning assembly according to one embodiment of the present invention and illustrated in an operative position about an eyeball with a suction force applied thereto.
Figure 5:
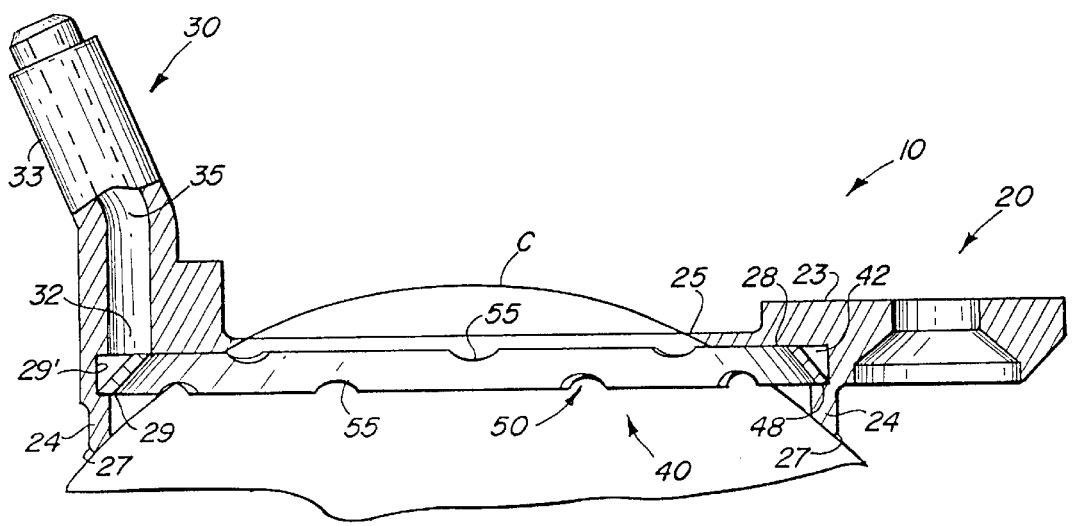
FIG. 5 is a partial cross sectional view of the improved positioning assembly according to another embodiment of the present invention and illustrated in an operative position about an eyeball with a suction force applied thereto.

Illustrated throughout the drawings, the present invention is directed generally towards a positioning assembly for improved retaining and positioning of the cornea of a patient's eye to be cut during a surgical operation, and is generally indicated by reference numeral 10 in FIGS. 4 and 5. More specifically, the present invention is directed towards suction enhancement means, 40, for improving and preserving the vacuum seal which attaches a positioning ring to the patient's eye during surgery. It will be understood that although the positioning assembly 10 of the present invention is likely to be used in conjunction with a microkeratome device, the latter does not form a part of the present invention.

The positioning assembly 10 of the present invention is directed for use with and may comprise a positioning ring 20, also known as an eyeball positioning ring, as illustrated in FIGS. 4 and 5. The positioning ring 20 is used to centrate the eye, that is, to retain, position and properly present the cornea of a patient's eyeball in a precise and aligned manner for surgery. Thus, the positioning ring 20 has a main body 22 which includes and defines an aperture 25 therein. The aperture 25 is sized to receive and permit the cornea C, of the eye to pass therethrough so as to expose the cornea, and a pre-determined depth thereof, for cutting during surgery. Typically, the cornea will be cut during surgery when a microkeratome with a cutting element is moved over the face of the positioning ring 20 and thus, over the exposed cornea, C, which as is clear from the drawings, protrudes through aperture 25. The positioning ring 20 is formed of a rigid material and preferably, a metallic material. Ideally, however, the positioning ring 20 will be made of a high grade stainless steel, which enhances precision engagement with the eyeball, can be formed to have a smooth, safe and glare-retardant surface finish, and which provides for ease of sterilization.

As illustrated in the drawings, the main body 22 of positioning ring 20 may be defined by a generally circular shape about the aperture 25, although it will be appreciated that it could be formed to have another shape, such as a square, rectangular, hexagonal or other shape about the aperture 25, and still function for the intended purpose. In the preferred embodiment, the main body 22 of the positioning ring 20 comprises a retention plate 23, which includes the aperture 25 defined therein, and a flange member 24 extending generally downwardly from the retention plate 23 and defining a generally open bottom side to main body 22. Ideally, the flange member 24 is disposed in spaced apart, generally surrounding relation to the aperture 25 defined in the retention plate 23. Also in the preferred embodiment, the flange member 24 of main body 22 preferably includes a lower edge 27 which is structured and disposed to engage the portion of the eye about the cornea in a fluid impervious manner. Similarly, and as illustrated in FIGS. 4 and 5, the retention plate 23 preferably includes an interior rim 26 disposed in surrounding relation about the aperture 25, which is structured to engage the eye disposed therein, also in a fluid impervious manner. It will therefore be appreciated that upon the positioning ring 20 being disposed in engaging relation with the eye, that an effective, generally air-tight seal can be achieved about the eyeball between retention plate 23 and flange member 24.

The positioning assembly of the present invention is further directed for use with and may comprise suctioning means 30 for attaching the positioning ring 20 to the eye on which surgery is to be performed. Preferably, the suctioning means 30 comprise a vacuum port 32 formed in positioning ring 20 and a vacuum means (not shown) for providing a suction force. The vacuum means are structured to apply a suction force which is sufficient to attach the positioning ring 20 to the eyeball about the cornea, C, and cause the cornea to be urged upwardly and to protrude through the aperture 25 of the positioning ring 20, and while not being so strong as to cause damage to the eyeball. It will be appreciated from the drawings that the vacuum port 32 formed in positioning ring 20 is operably coupled to and in fluid flow communication with the vacuum means such that the suction force is applied therethrough. In a preferred embodiment, a tubular connection member 33 extends from the positioning ring 20 in fluid flow communication via an internal vacuum passage 35, with the vacuum port 32. Connection member 33 is adapted to be interconnected with a vacuum hose (not shown) which in turn may be connected to the vacuum means such that when the vacuum means are activated, the suction force is applied through the vacuum port 32. In the preferred embodiment, the vacuum port 32 is disposed at an undersurface 28 of positioning ring 20 either through retention plate 23 or flange member 24. Thus, the vacuum port 32 is disposed to provide a suction force, once the vacuum means are activated, to a point radially exterior of the aperture 25 and radially interior of the flange member 24, so as to form a seal about the cornea of the eye about to undergo surgery. It should be clear at this point that the structure of positioning ring 20, when accompanied by a suction force, acts to properly position and align the cornea C, for surgery and to generally maintain that position during surgery. Typically, a vacuum of about 25 inches of Hg at sea level will be used.

Figure 3A:
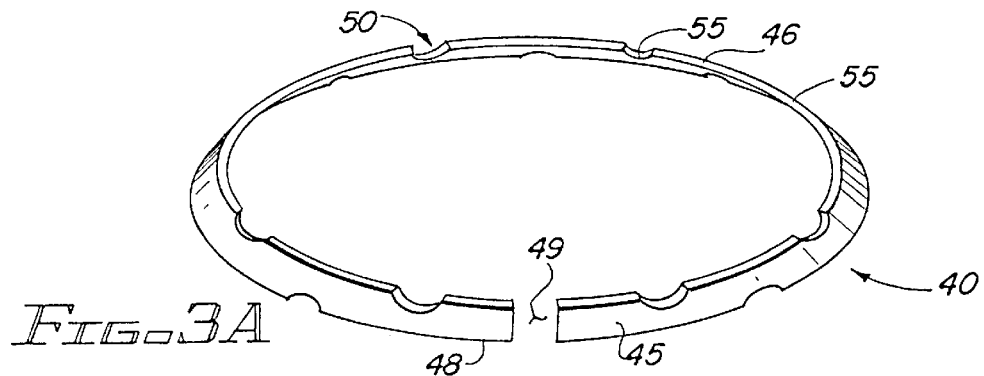
FIG. 3-A is a front view of the suction enhancement means of the present invention in a more preferred embodiment.
Figure 3B:
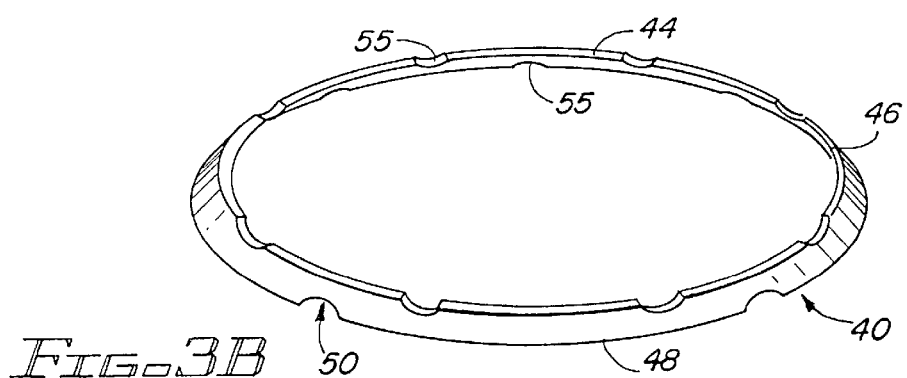
Figure 3C:
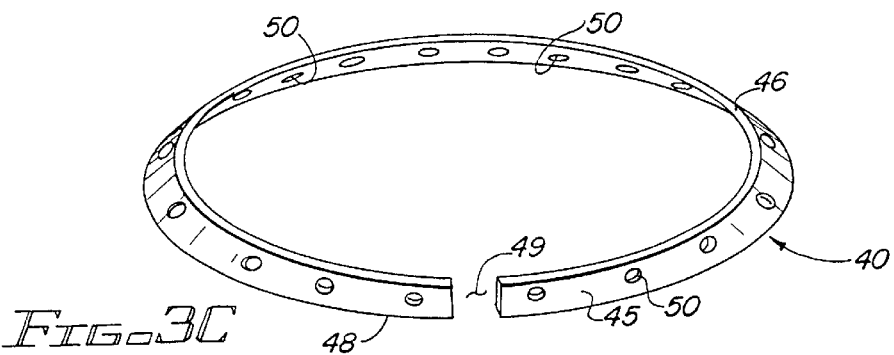

Referring now to FIGS. 3–5, the positioning assembly 10 of the present invention is seen to comprise suction enhancement means 40. The suction enhancement means 40 preferably include a suction enhancement member 44, which in the preferred embodiment comprises a segment 45 formed of a resilient material. The resilient material segment 45, which can be formed from a metallic material such as aluminum or stainless steel, is preferably formed from a suitable plastic material to provide for ease of manufacture and economical disposal. Further, resilient material segment 45 has a thickness of between generally about three-tenths (0.3 mm) of a millimeter to generally about five-tenths (0.5 mm) of a millimeter. Accordingly, the resilient material segment 45 will take up minimal space within the positioning ring 20 and consequently, will not mis-align nor displace the positioning ring 20 relative to the eye.

As best illustrated in FIGS. 4 and 5, the suction enhancement means 40, preferably in the form of the resilient material segment 45, is disposed within undersurface 28 of the positioning ring 20 and at least partially between the suctioning means 30 operably coupled to the positioning ring 20, and the portion of the eye surrounding the cornea to be cut. More specifically, the suction enhancement means 40 are structured to be disposed between the vacuum port 32 of the positioning ring 20 and the eyeball to be cut during surgery. In the preferred embodiment, the resilient material segment 45 is structured to be disposed in fitted engagement within the positioning ring 20 about a region which is radially interior of the flange member 24. The suction enhancement means 40, are additionally structured and disposed to engage the positioning ring 20 so as to define a suction channel 42 between the positioning ring 20 and the suction enhancement member, such as segment 45, itself. Preferably, the suction enhancement member 44 comprises a generally ring like configuration, as illustrated in FIG. 3-B, so as to extend substantially or completely about the aperture 25 defined in the main body of the positioning ring 20. By extending at least substantially about the aperture 25, the suction channel 42 defined by the suction enhancement member 44 also extends at least substantially about the eyeball.

The suction channel 42 is disposed in fluid flow communication with the suctioning means 30, and preferably, with the vacuum port 32 defined in the positioning ring 20. Further, the suction enhancement means 40 include at least one suction port 50 formed in suction enhancement member 44, such as segment 45, and which extends into fluid flow communication with the suction channel 42. In a preferred embodiment, the suction enhancement means 40 include a plurality of suction ports 50, ideally disposed throughout the length of resilient material segment 45 SO as to extend at least substantially about the eyeball. Accordingly, upon actuation of the vacuum means, a suction force is applied through the vacuum port 32, to the suction channel 42, and further, through the suction ports 50 so as to distribute the suction force more uniformly about the entire eyeball. As a result, the positioning ring 20 is likely to possess an improved ability to remain attached to the eyeball during surgery.

The suction enhancement means 40 are additionally structured to maintain a flow-through-integrity of the suction channel 42 upon actuation of the vacuum means and the resulting attachment of the positioning ring 20 to the eyeball. Specifically, as the suction force is applied to the assembly, the interoccular pressure within the eye bulges so as to urge the eye upwardly and into the positioning ring 20. The suction enhancement means 40 are therefore, structured to resist collapse, and to thereby, maintain the flow-through-integrity of suction channel 42. To achieve this, the suction enhancement means 40, preferably in the form of segment 45, is formed to have an outward taper from top edge 46 to bottom edge 48 of the segment 45, as is perhaps best illustrated in FIGS. 3-A to 3-C. In the preferred embodiment, the outward taper of the segment 45 is between generally about thirty (30) and forty (40) degrees, and ideally, thirty-five (35) degrees between the top and bottom edges, 46, 48. Thus, the segment 45 is sized and structured to be angularly disposed in fitted engagement with the positioning ring 20 and includes a height dimension which is sufficient to extend between an undersurface 28 of the retention plate 23 and the flange member 24 of the positioning ring 20. More specifically, and illustrated in FIGS. 4–5, the top edge 46 of the segment 45 is structured to engage the retention plate 23, and the bottom edge 48 is structured to engage the flange member 24 of the positioning ring 20 so as to define the suction channel 42. As such, the material construction of the segment 45, along with engagement of its top and bottom edges 46, 48 with the positioning ring 20 prevents inward buckling as the cornea of the eye bulges upwardly and into position within aperture 25. In particular, even though the segment 45 is generally thin, it is seen that because of the small height dimension required to bridge the distance between flange member 24 and retention plate 23, it is nonetheless sufficient to resist inward buckling.

Figure 1:
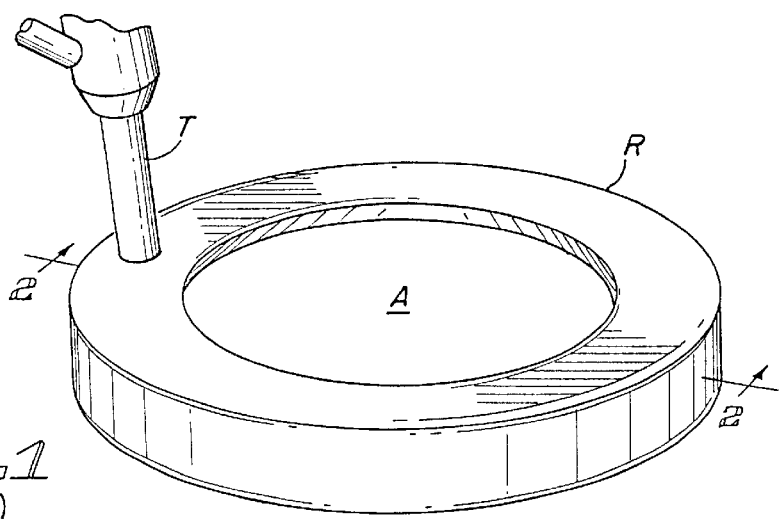
FIG. 1 is a perspective view of a common type of suction ring in communication with a hollow suction tube for applying a vacuum thereto.
Figure 2:
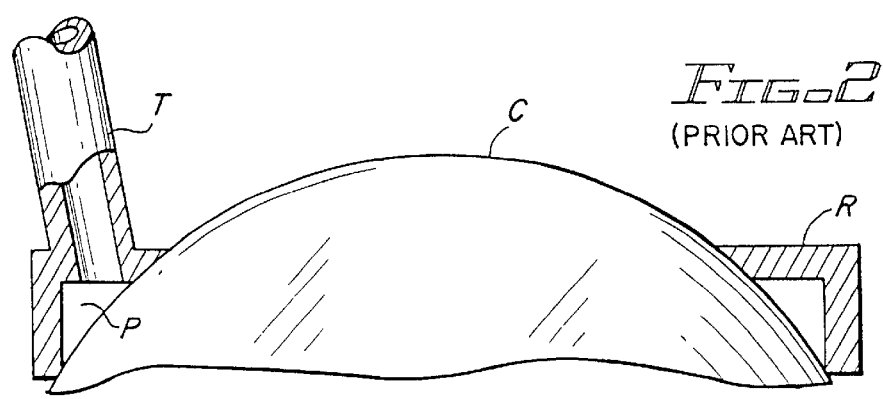
FIG. 2 is a partial cross sectional view of the suction ring device taken along the lines 2—2 illustrated in FIG. 1 and depicting an operative position about a cornea, C, with a suction force applied thereto.

In this regard, the resilient material segment 45 may be structured and disposed so as to frictionally engage the positioning ring 20, so as to be directed for use with available suction ring devices such as illustrated in FIGS. 1–2. In a more preferred embodiment, however, the flange member 24 of the positioning ring 20 includes an interiorly disposed ridge 29 formed thereon which is sized and structured to receive the bottom edge 48 of the enhancement segment supportably thereon, as illustrated in FIGS. 4 and 5. Specifically, the ridge 29, which may include an inwardly defined protrusion, is preferably defined by an interiorly disposed groove 29' that extends about the inner periphery of flange member 24. The groove 29' is sized and structured to receive the bottom edge 48 of the segment 45 therein. As such, a smooth and even contour is maintained at a portion of the positioning ring 20 which may engage the eye, and the segment 45 is recessed within the positioning ring 20 to further minimize a risk of displacing the eye relative to the positioning ring 20.

Also in the preferred embodiment, the suction ports 50 of the segment 45 have an inner diameter which, while sized to permit gentle gripping about the eyeball once a suction force has been activated, is not so large as to sacrifice or weaken the structural integrity of the suction enhancement member. Ideally, the suction ports 50 will comprise a plurality of indentations or cut-out portions 55 formed along the top edge 46 and bottom edge 48 of the resilient material segment 45 so as to maintain an overall strength of the segment 45.

It will be appreciated from the foregoing that the suction enhancement means 40 of the present invention are structured and disposed to act as a barrier to significantly prevent blockage of the suction force being applied to the assembly 10. As has been described, when a suction force is applied to the eyeball during surgery, a mucous membrane about the eyeball, known as conjunctiva, may be drawn inwardly towards the vacuum port 32 of the positioning ring 20 and may result in the suction force being partially or completely blocked. In the preferred embodiment wherein the suction ports 50 are disposed throughout segment 45, which itself is disposed about the eyeball, the suction force is effectively distributed substantially three hundred and sixty degrees about the eyeball, such that a concentrated suction force which would tend to draw in the conjunctiva, is not present. Although the suction force is more evenly distributed, it is still sufficient to securely grasp the eye, but insufficient to draw in conjunctiva. Thus, the segment 45 is structured and disposed to prevent both partial and complete occlusion of the suction force applied via the vacuum port 32. In addition, however, the suction enhancement means 40 act as a barrier to limit, if not prevent altogether, the entry of mucus from the eye into the suction channel 42 and the internal vacuum passages 32, 35 of the positioning ring. This factor also helps to ensure that the suction force will not become occluded eventually by the accumulation of mucus in the internal vacuum passages of the positioning ring.

In the preferred embodiment, the suction enhancement means 40 are structured and disposed to removably engage the positioning ring 20 so as to facilitate cleaning of the positioning ring 20 for subsequent use on another patient. As an initial matter, the suction enhancement means 40 of the present invention maintain the positioning ring in a cleaner condition than is presently known in the art because mucus from the eye is substantially prevented from entering into the suction channel 42 and internal vacuum passages of the positioning ring. On the other hand, the suction enhancement means 40 are likely to have contacted the eye's mucous tissue during surgery. To avoid additional cleaning, in the preferred embodiment, the suction enhancement means 40 in the form of the resilient material segment 45, is structured and disposed to be removable from the positioning ring 20, whereupon it can be safely and easily disposed of. It will be appreciated that by removing the resilient material segment 45 from the positioning ring 20, the under surfaces of the positioning ring 20 are easily accessible for cleaning and sterilization. Additionally, the resilient material segment 45 is preferably formed of a suitably resilient plastic material that is sufficiently flexible to be temporarily compressed, so as to facilitate introduction and removal of the segment 45 into and out of engagement with the positioning ring 20, with minimal risk of causing damage to the positioning ring 20. In a more preferred embodiment, resilient material segment 45 may be structured to include a gap 49 defined therein which permits a diameter of the generally circular shape formed by the segment 45 to be temporarily compressed during introduction and removal of the segment 45 from positioning ring 20. In this embodiment, when the segment 45 is disposed in an operative position within positioning ring 20, the gap 49 may itself define a suction port 50 in that the segment 45 will generally not completely encircle the eyeball, and may in fact, only extend partially thereabout. Of course, while segment 45 is sufficiently flexible for temporary compression, it is also sufficiently rigid so as to not itself be sucked out of position, and further, so as to have an elastic memory sufficient to return the segment 45 towards its normal, at rest position, and thereby, maintain segment 45 securely in place within the positioning ring 20. In this regard, it should be understood that segment 45 may be formed to include a biasing force to be exerted by the segment 45 on the flange member 24 which is sufficient to retain the segment 45 in fitted engagement within the flange member 24. Alternatively, the segment 45 does not necessarily have to include a biasing force as in one embodiment, interiorly disposed ridge 27 on flange member 24 may be sufficient to retain segment 45 in fitted engagement with positioning ring 20.

Since many modifications, variations and changes in detail can be made to the described preferred embodiment of the invention, it is intended that all matters in the foregoing description and shown in the accompanying drawings be interpreted in the illustrative and not in a limiting sense. Thus, the scope of the invention should be determined by the appended claims and their legal equivalents.

Now that the invention has been described,

What is claimed is:

1. A positioning assembly for retaining and positioning a cornea of a patient's eye for cutting during a surgical operation, said assembly comprising:

a) a positioning ring having an aperture sized to receive and expose the cornea therethrough, said positioning ring including a vacuum port connected to and in fluid communication with a vacuum means for providing a suction force sufficient to temporarily attach said positioning ring to the eyeball about the cornea, b) a suction enhancement member including a segment structured and disposed to engage the positioning ring, so as to be disposed at least partially between said vacuum port of said positioning ring and the eyeball to be cut during surgery;

c) said segment including at least one suction port and being structured to engage said positioning ring so as to define a suction channel between said positioning ring and said segment;

d) said suction channel being disposed in fluid flow communication with said vacuum port of said positioning ring such that upon actuation of the vacuum means, the suction force is applied through said vacuum port and to said suction channel; and e) said segment being structured to maintain a flow-through integrity of said suction channel upon actuation of the vacuum means and temporary attachment of the positioning ring to the eyeball.

2. A positioning assembly as recited in claim 1 wherein said segment is structured to removably engage the positioning ring.

3. A positioning assembly as recited in claim 1 wherein said suction force is applied to the eyeball through said at least one suction port in said segment.

4. A positioning assembly as recited in claim 1, wherein said segment is structured to substantially surround the aperture of the positioning ring such that said suction channel extends substantially about the eyeball.

5. A positioning assembly as recited in claim 4 wherein said segment includes a plurality of said suction ports disposed throughout said segment, said suction ports being structured and disposed to permit the suction force to be applied therethrough, substantially about the eyeball, thereby enhancing the attachment of the positioning ring to the eyeball.

6. To be utilized to retain and properly expose and align a cornea of an eye during eye surgery, an improved eye positioning assembly comprising:

(i) a positioning ring, said positioning ring being substantially rigid and comprising:

a retention plate, said retention plate including an aperture defined therein and structured to receive the cornea of the eye therein, said retention plate further including an interior rim disposed in surrounding relation about said aperture and structured to engage the eye disposed therein, a flange member extending generally downwardly from said retention plate in spaced apart, generally surrounding relation to said aperture in said retention plate, a lower edge of said flange member being structured to engage the eye, a vacuum port disposed in fluid flow communication with a point radially interior of said flange member, and vacuum means connected with said vacuum port and structured to provide a suction through said vacuum port, said suction being sufficient to secure said interior rim of said retention plate and said lower edge of said flange member to the eye such that the cornea of the eye is urged upwardly and protrudes through said aperture defined in said retention plate and is retained therein; and (ii) a suction enhancement member, said suction enhancement member comprising:

a segment structured for fitted engagement with said positioning ring radially interior of said flange member, said segment being structured and disposed to define a suction channel between said suction enhancement member and said positioning ring, at least one suction port defined in said segment and extending into fluid flow communication with said suction channel, said suction channel also being disposed in fluid flow communication with said vacuum port of said positioning ring such that said suction produced by said vacuum means acts on the eye through said at least one suction port defined in said segment, and said segment being structured to resist a collapse thereof towards said positioning ring upon an interior surface of said segment engaging the eye, thereby maintaining a flow through integrity of said suction channel.

7. An improved eye positioning assembly as recited in claim 6 wherein said segment is formed of resilient material.

8. An improved eye positioning assembly as recited in claim 7 wherein said segment includes a generally ring like configuration structured to extend substantially about said aperture defined in said retention plate.

9. An improved eye positioning assembly as recited in claim 8 wherein said segment includes a gap defined therein and structured to permit a diameter of said segment to be temporarily compressed, thereby facilitating introduction and removal of said segment into and out of said engagement with said positioning ring.

10. An improved eye positioning assembly as recited in claim 9 wherein said gap is further structured to define said at least one suction port.

11. An improved eye positioning assembly as recited in claim 10 further including a plurality of said suction ports disposed along a length of said segment, thereby providing suction substantially about an entire perimeter of the eye.

12. An improved eye positioning assembly as recited in claim 8 wherein said segment is further structured to permit a diameter thereof to be temporarily compressed, thereby facilitating introduction and removal of said segment into and out of said engagement with said positioning ring.

13. An improved eye positioning assembly as recited in claim 8 further including a plurality of said suction ports disposed along a length of said segment, thereby providing suction substantially about an entire perimeter of the eye.

14. An improved eye positioning assembly as recited in claim 13 wherein said suction ports include a plurality of indentations defined along a top edge and a bottom edge of said segment and structured to maintain an overall strength of said segment.

15. An improved eye positioning assembly as recited in claim 14 wherein said segment includes and outward taper from said top edge to said bottom edge thereof.

16. An improved eye positioning assembly as recited in claim 15 wherein said outward taper is between generally about thirty (30) and forty (40) degrees.

17. An improved eye positioning assembly as recited in claim 15 wherein said outward taper is generally about thirty-five (35) degrees.

18. An improved eye positioning assembly as recited in claim 6 wherein said segment is structured to removably engage said positioning ring so as to facilitate effective cleaning of said positioning ring.

19. An improved eye positioning assembly as recited in claim 18 wherein a thickness of said segment is between generally about three-tenths (0.3 mm) and five-tenths (0.5 mm) millimeters.

20. An improved eye positioning assembly as recited in claim 18 wherein said flange member of said positioning ring includes means to secure said segment in said removable engagement with said positioning ring.

21. An improved eye positioning assembly as recited in claim 20 wherein said means to secure said segment includes an interior ridge disposed on said flange member of said positioning ring and structured to engage said bottom edge of said segment.

22. An improved eye positioning assembly as recited in claim 20 wherein said means to secure said segment includes an interior groove defined in said flange member of said positioning ring and structured to receive said bottom edge of said segment therein.

23. An improved eye positioning assembly as recited in claim 6 wherein said segment is structured to extend between said retention plate and said flange member of said positioning ring.

24. An improved eye positioning assembly as recited in claim 23 wherein said segment includes a top edge and a bottom edge, said bottom edge being structured to engage said flange member and said top edge being structured to engage said retention plate so as to define a suction channel between said suction enhancement member and said positioning ring.

25. An improved eye positioning assembly as recited in claim 6 wherein said suction member is disposable.

26. An improved eye positioning assembly as recited in claim 6 wherein said vacuum port is defined in said retention plate of said positioning ring and is structured to be in partial fluid flow communication with said suction channel.

* * * * *